United States Patent
Henschke et al.

(10) Patent No.: US 8,212,021 B2
(45) Date of Patent: Jul. 3, 2012

(54) PROCESS FOR MAKING 5-AZACYTOSINE NUCLEOSIDES AND THEIR DERIVATIVES

(75) Inventors: Julian Paul Henschke, Harlow (GB); Xiaoheng Zhang, Kunshan (CN); Lunghu Wang, Kaohsiung (TW); Yung Fa Chen, Tainan County (TW)

(73) Assignee: ScinoPharm Taiwan, Ltd., Tainan (TW)

( * ) Notice: Subject to any disclaimer, the term of this patent is extended or adjusted under 35 U.S.C. 154(b) by 421 days.

(21) Appl. No.: 12/538,271

(22) Filed: Aug. 10, 2009

(65) Prior Publication Data

US 2010/0036112 A1 Feb. 11, 2010

Related U.S. Application Data

(60) Provisional application No. 61/188,431, filed on Aug. 8, 2008.

(51) Int. Cl.
*C07H 19/12* (2006.01)
(52) U.S. Cl. .................................................. 536/28.3
(58) Field of Classification Search .................. None
See application file for complete search history.

(56) References Cited

U.S. PATENT DOCUMENTS

| | | | |
|---|---|---|---|
| 3,350,388 A | 10/1967 | Sôrm et al. | |
| 4,082,911 A | 4/1978 | Vorbruggen | |
| 4,209,613 A | 6/1980 | Vorbruggen et al. | |
| 6,887,855 B2 | 5/2005 | Ionescu et al. | |
| 6,943,249 B2 | 9/2005 | Ionescu et al. | |
| 7,038,038 B2 | 5/2006 | Ionescu et al. | |
| 2006/0247432 A1 | 11/2006 | Onescu et al. | |

FOREIGN PATENT DOCUMENTS

| | | |
|---|---|---|
| DE | 1922702 | 11/1969 |
| DE | 2012888 | 9/1971 |
| WO | WO2009/047314 | 4/2009 |

OTHER PUBLICATIONS

Daskalakis et al., "Demethylation of a hypermethylated P15/INK4B gene in patients with myelodysplastic syndrome by 5-Aza-2'—deoxycytidine (decitabine) treatment" Blood (2002) vol. 100 No. 8 pp. 2957-2964.*

Nomura et al., "Nucleosides and nucleotides. Part 212: Practical large-scale synthesis of 1-(3-C-ethynyl-beta-D-ribo-pentofuranosyl)cytosine (ECyd), a potent antitumor nucleoside. Isoburyryloxy group as an efficient anomeric leaving group in the Vorbruggen glycosylation reaction" Tetrahedron (2002) vol. 58 pp. 1279-1288.*

Corey et al., A total synthesis of (+−)-Fumagillin, *J. Am. Chem. Soc.*, 1972, vol. 94 pp. 2549-2550.

International Preliminary Report on Patentability dated Aug. 31, 2010.

A. Piskala et al., Direct Synthesis of a 5-Azapyrimidine Ribonucleoside by the Trimethylsilyl Procedure, *Nucl. Acid Chem.*, (1978), 1, 435-449.

Vorbrüggen et al., Nucleoside Synthesis with Trimethylsilyl Triflate and Perchlorate as Catalysts, *Chem. Ber.* 114, 1234-1255 (1981).

Kissinger et al., Determination of the Antileukemia Agents Cytarabine and Azacitidine and Their Respective Degradation Products by High-Performance Liquid Chromatography, *Journal of Chromatography*, 353 (1986) 309-318.

John A. Beisler, Isolation, Characterization, and Properties of a Labile Hydrolysis Product of the antitumor Nucleoside, 5-Azacytidine, *Journal of Medicinal Chemistry*, 1978, vol. 21, No. 2.

Winkley et al., Direct Glycosylation of 1,3,5-Triazinones. A New Approach to the Synthesis of the Nucleoside Antibiotic 5-Azacytidine (4- Amino-1β-D-ribofuranosy1-1,3,5-triazin-2-one) and Related Derivatives, *Direct Glycosylation of 1,3,5-Triazinones*, vol. 35, No. 2, (1970).

Niedballa et al., A General Synthesis of N-glycosides. V.[1,2] Synthesis of 5- Azacytidines, *J. Org. Chem.*, vol. 39, No. 25, (1974).

Niedballa et al., A General Synthesis of N-Glycosides. I.[1] Synthesis of Pyrimidine Nucleosides, *J. Org. Chem.*, vol. 39, No. 25 (1974).

J. Ben-Hattar et al., An Improved Synthesis of 2'-Deosy-5-azacytidine by Condensation of a 9-Fluorenylmethoxycarbonyl-Protected Sugar onto the Silylated Base, *J. Org. Chem.*, 51, 3211-3213 (1986).

Piskala et al., Synthesis of 1-Glycosyl Derivatives of 5-Azauracil and 5- Azacytosine, *Nucleic Acids Components and Their Analogues*. (1964).

* cited by examiner

*Primary Examiner* — Eric S Olson

(57) ABSTRACT

A process of synthesizing a 5-azacytosine nucleoside, such as azacitidine and decitabine, comprises coupling a silylated 5-azacytosine with a protected D-ribofuranose of formula in the presence of a sulfonic acid catalyst.

23 Claims, No Drawings

PROCESS FOR MAKING 5-AZACYTOSINE NUCLEOSIDES AND THEIR DERIVATIVES

RELATED APPLICATIONS

This application claims priority from U.S. Provisional Patent Application Ser. No. 61/188,431 which was filed on Aug. 8, 2008. The entire content of which is herein incorporated as reference.

BACKGROUND OF THE INVENTION

1. Field of the Invention

The present invention relates to the efficient commercial synthesis of 1-glycosyl-5-azacytosines, hereafter referred to as 5-azacytosine nucleosides. The inventive methods are particularly useful in preparing 5-azacytosine nucleosides such as 5-azacytidine (azacitidine), 2'-deoxy-5-azacytidine(decitabine). It is well known that azacitidine and its ribodeoxy derivative decitabine are useful in the treatment of disease, especially for myelodysplastic syndrome (MDS).

2. Description of the Related Arts

Examples of 5-azacytosine nucleosides and their syntheses have previously been reported. Azacitidine (also known as 5-azacytidine, 5-AC and Vidaza™) and its ribodeoxy derivative decitabine (also known as 2'-deoxy-5-azacytidine, 5-aza-2'-deoxycytidine, DAC, Dacogen®) were first synthesized as potential chemotherapeutic agents for cancer. A number of methods have been developed to make them but these methods, on the whole, are inefficient and less desirable for commercial production. One important problem is that when the 5-azacytosine ring (s-triazine ring) is conjugated to a carbohydrate, it is sensitive to decomposition by water (under neutral, basic and acidic conditions) and in fact undergoes facile hydrolysis in aqueous formulations, in aqueous emulsions, in aqueous solutions and when exposed to moisture in aqueous work-up during synthesis making commercial manufacture challenging.[1],[13] Therefore it is desirable to develop a production process which limits or avoids the contact of these nucleosides with water.

See, e.g., the following references:

(1) J. A. Beisler, *J. Med. Chem.*, 1978, 21, 204.
(2) U.S. Pat. No. 3,350,388 (1967) and DE1922702 (1969), Šorm and Pískala (Ceskosl Ovenska Akademieved); A. Pískala and F. Šorm, *Collect. Czech. Chem. Commun.* 1964, 29, 2060.
(3) M. W. Winkley and R. K. Robins, *J. Org. Chem.*, 1970, 35, 491.
(4) A. Pískala and F. Šorm, *Nucl. Acid Chem.*, 1978, 1, 435.
(5) DE2012888 (1971), Vorbrüggen and Niedballa (Schering A G).
(6) U. Niedballa and H. Vorbrüggen, *J. Org. Chem.*, 1974, 39, 3672-3674.
(7) U.S. Pat. No. 7,038,038 (2006), Ionescu and Blumbergs (Pharmion Corporation).
(8) H. Vorbrüggen, K. Krolikiewicz and B. Bennua, *Chem. Ber.*, 1981, 114, 1234-1255.
(9) U.S. Pat. No. 4,082,911 (1978), Vorbrüggen (Schering Aktiengesellschaft).
(10) U.S. Pat. No. 6,887,855 (2005), Ionescu and Blumbergs and Silvey (Pharmion Corporation, Ash Stevens, Inc.).
(11) U.S. Pat. No. 6,943,249 (2005), Ionescu and Blumbergs and Silvey (Ash Stevens, Inc., Pharmion Corporation).
(12) J. Ben-Hatter and J. Jiricny, *J. Org. Chem.*, 1986, 51, 3211-3213.
(13) L. D. Kissinger and N. L. Stemm, *J. Chromatography*, 1986, 353, 309-318.
(14) U. Niedballa and H. Vorbrüggen, *J. Org. Chem.*, 1974, 39, 3654-3660.

The entire content of each of the above references is incorporated herein as reference.

Pískala and Šorm[2] teach a lengthy method for the synthesis of azacitidine and decitabine which involves the use of reactive N-glycosylisocyanate intermediates possessing 1-β-configuration. The synthetic process (Scheme 1) comprises reacting a peracylglycosyl isocyanate with an S-alkylisothiurea to obtain a peracylglycosylisothiourea, condensing the latter with an orthoester of an aliphatic acid at high temperature (135° C.) to obtain hydroxy-protected glycosyl-4-alkylmercapto-2-oxo-1,2-dihydro-1,3,5-triazines followed by deprotection with ammonia ($NH_3$) in methanol (MeOH) in a sealed vessel over a 12-24 hour period. Although based on the isocyanate, the overall yield of azacitidine is 43% and the overall yield of decitabine is 33%, it could be difficult to store the isocyanate and its use might provide a health risk. The route also suffers from other difficult to scale-up steps, including the use of the carcinogenic ICH Class I solvent benzene, and the need for a pressure vessel in the deprotection step.

Scheme 1-Isocyanate Method for synthesis of 5-azacytidines

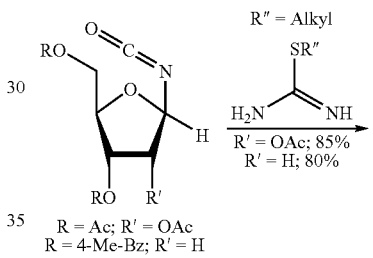

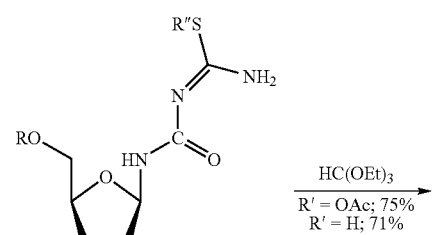

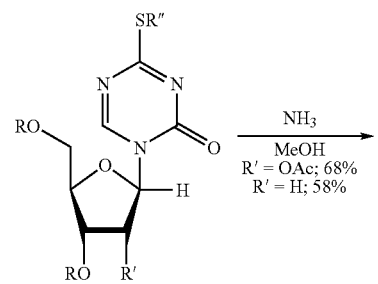

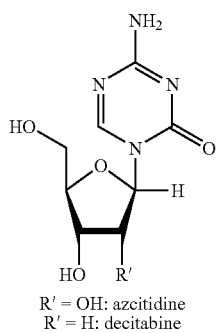

R' = OH: azcitidine
R' = H: decitabine

Another potential process for azacitidine and decitabine was reported by Winkley and Robins[3] (Scheme 2). Their approach utilizes the non-catalysed coupling of 1-halosugars with 2-[(trimethylsilyl)amino]-4-[(trimethylsilyl)oxy]-s-triazine(silyl 5-azacytosine) which probably proceeds via an $S_N2$ mechanism. Pískala and Šorm[4] also reported a similar process utilizing a 1-chlorosugar for the synthesis of azacitidine (Scheme 2), which suffers from the need for gaseous hydrogen chloride in the synthesis of the 1-chlorosugar, very low overall yields (azacitidine in 11%, and decitabine in 7% overall yield[3]), long reaction times (3-7 days), the need for pressure vessels in the deprotection step, the instability of the halosugars, complicated column chromatography and lengthy work-up and isolation procedures.

Scheme 2-Use of 1-halosugars in the synthesis of azacitidine and decitabine

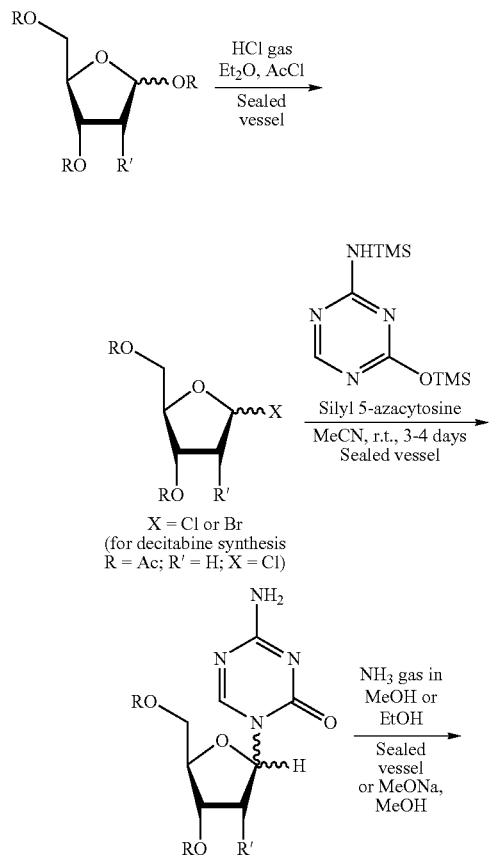

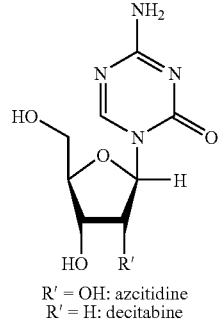

R' = OH: azcitidine
R' = H: decitabine

Niedballa and Vorbrüggen[5,6] teach the synthesis of protected (blocked) nucleosides including azacitidine and decitabine that utilizes a large amount of tin chloride in dichloroethane (DCE) or acetonitrile (MeCN) to promote the coupling of 5-azacytosine and protected sugar moieties (Scheme 3). According to Ionescu and Blumbergs[7] there are a number of major drawbacks to this process: first, removal of tin from the API is difficult Second, emulsions developed during the workup of the coupling mixture. Third, a difficult filtration step needs to be performed in order to isolate the insoluble tin salts. For these reasons it should be concluded that this process is not suitable for the commercial manufacture of azacitidine.[7]

Scheme 3-Synthesis of protected azacitidine and decitabine using Vorbrüggen's coupling method

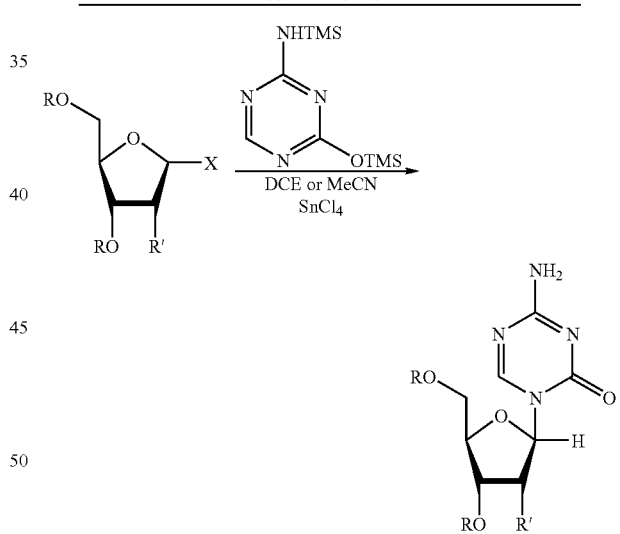

When R' = OAc or OBz, R = Ac or Bz and X = OAc
When R' = H, R = 4-Me-Bz or Fmoc
50-81% when R = Ac or Bz; R' = OAc or OBz; X = β-OAc
41% when R = 4-Me-Bz; R' = H; X = α-Cl
21% when R = Fmoc; R' = H; X = α-, β-Cl Vorbrüggen[9] teaches a general method for the coupling of silylated bases and nucleoside bases (including cytosine, pyridines triazoles, and pyrimidines, but not 5-azacytosine) with protected 1-O-acyl, 1-O-alkyl or 1-halosugars (viz., ribose, deoxyribose, arabinose and glucose derivatives) in benzene, DCE or MeCN to make protected nucleosides (Scheme 4). The coupling is promoted by trimethylsilyl (TMS) esters of esterifiable mineral acids or strong sulfonic acids, including trimethylsilyl triflate (TMSOTf), TMSO- ClO₃ and TMSOSO₂F. The requirement for an aqueous workup makes this method less than desirable for synthesis of azacitidine and decitabine.

Scheme 4-Vorbrüggen's coupling protocol utlizing trimethylsilyl esters of strong acids

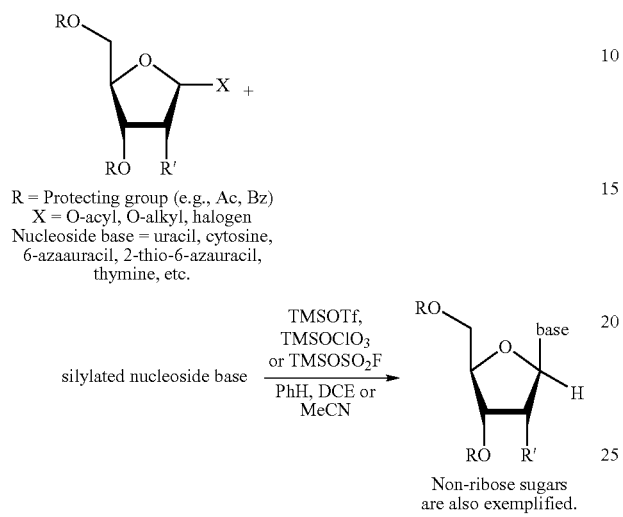

R = Protecting group (e.g., Ac, Bz)
X = O-acyl, O-alkyl, halogen
Nucleoside base = uracil, cytosine, 6-azauracil, 2-thio-6-azauracil, thymine, etc.

Non-ribose sugars are also exemplified.

Ionescu and Blumbergs[7] teach a manufacturing process (Scheme 5) specifically for the synthesis of azacitidine which is based on the general trimethylsilyl ester promoted coupling methodology invented by Vorbrüggen.[9] Silylation of 5-azacytosine is conducted using an excess of hexamethyldisilizane (HMDS) and a catalytic amount of ammonium sulfate. The 1-O-acyl-carbohydrate and silylated nucleoside base coupling reaction is carried out in a "solvent having low water solubility" such as dichloromethane (DCM) in the presence of a greater than stoichiometric amount of the non-metallic Lewis acid catalyst TMSOTf. An aqueous workup is employed and a number of costly steps are necessary to remove harmful water and switch solvents into suitable conditions for the deprotection step.

Scheme 5-An azacitidine manufacturing method

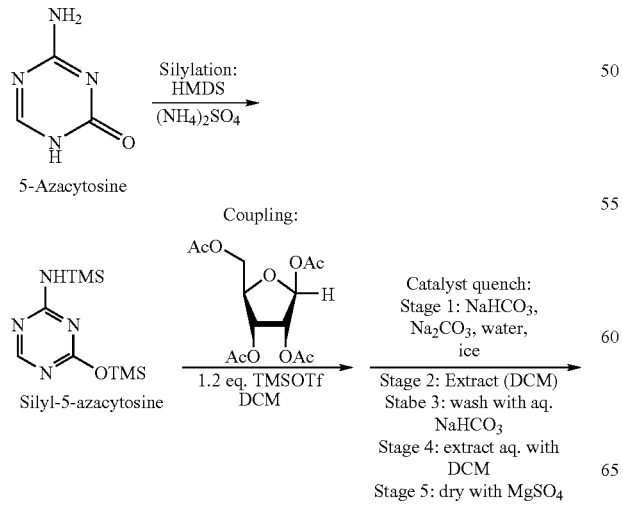

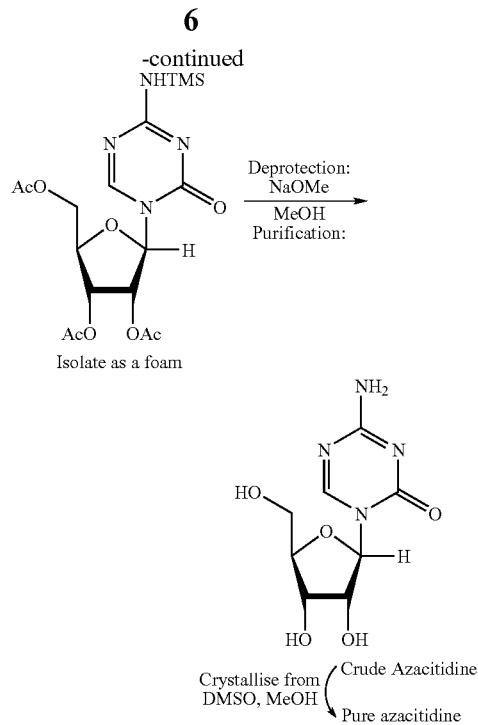

Isolate as a foam

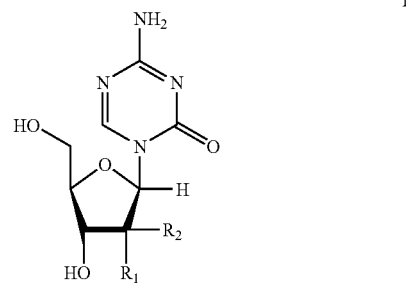

Crystallise from DMSO, MeOH → Crude Azacitidine / Pure azacitidine

Therefore, there is a need for a more efficient process for manufacturing a 5-azacytosine nucleoside compound on a large scale.

SUMMARY OF THE INVENTION

In accordance with one aspect of the present application, a process for the preparation of a 5-azacytosine nucleoside compound of formula I:

I

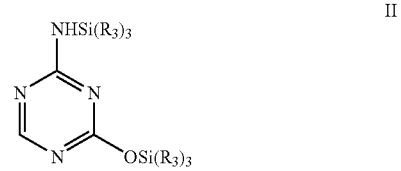

wherein $R_1$ is hydrogen, hydroxy or halogen; $R_2$ is hydrogen or halogen, comprises:

a) reacting 5-azacytosine with a silylating agent to produce a reaction mixture containing a silylated 5-azacytosine of formula II:

II wherein each of $R_3$ is independently optionally substituted $C_1$-$C_{20}$ alkyl group or aryl group.

b) coupling the silylated 5-azacytosine of formula II with a protected D-ribofuranose of formula III:

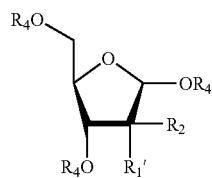

wherein $R_1'$ is hydrogen, halogen or $OR_4$; $R_4$ represents a hydroxyl protecting group; in a first organic solvent and in the presence of a sulfonic acid catalyst to obtain a liquid reaction mixture comprising protected 5-azacytosine nucleoside of formula IV:

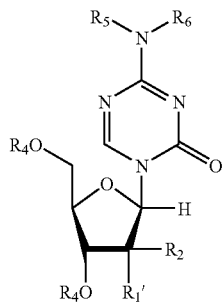

wherein each of $R_5$ and $R_6$ is independently hydrogen or $Si(R_3)_3$, and $R_3$, $R_1'$, and $R_2$ are as defined above; and c) converting the protected 5-azacytosine nucleoside of formula (IV) to the 5-azacytosine nucleoside of formula (I).

Preferably, the process described above is free of an aqueous work-up step to quench or remove the catalyst.

In accordance with another aspect of the present application, in the above-described process, the catalyst is not limited to a sulfonic acid and may be any suitable catalyst, but the process is free of an aqueous work-up step to quench or remove the catalyst.

In accordance with yet another aspect of the present invention, a process of making a 5-azacytosine nucleoside compound of formula (I), as described above, comprises: i) forming a homogenous solution comprising at least a polar aprotic solvent and a protected 5-azacytosine nucleoside of formula (IV) as described above in a polar aprotic solvent; and ii) converting the protected 5-azacytosine nucleoside of formula (IV) to the 5-azacytosine nucleoside of formula (I) in the homogenous solution. Preferably, prior to the step ii), this process is free of a step carried out in the presence of a substantial amount of water, e.g., less than 100% by weight of the compound of formula (IV), more preferably, less than 10% by weight of the compound of formula (IV), most preferably, less than 1% by weight of the compound of formula (IV).

As an embodiment, the forming step i) discussed above is preferably accomplished by adding a polar aprotic solvent to a previously existing solution comprising a protected 5-azacytosine nucleoside of formula (IV) and an organic solvent used during the reaction of making the protected 5-azacytosine nucleoside of formula (IV).

The $C_1$-$C_{20}$ alkyl group used herein may be a straight chain alkyl group, a branched alkyl group, or a cyclic alkyl group, preferably methyl.

The silylating agent used in the present invention can be any suitable agent, such as hexamethyldisilizane (HMDS), trimethylsilylchloride (TMSCl), N,O-bis(trimethylsilyl)acetamide (BSA), and N,O-Bis(trimethylsilyl)trifluoro acetamide (BSTFA) and trimethylsilyl triflate (TMSOTf). HMDS is the most preferred embodiment of the silyating agent of the present invention.

The hydroxyl protecting group $R_4$ may be any suitable group that can protect the hydroxyl group on a D-ribofuranose from unwanted reaction. For example, the hydroxyl protecting group $R_4$ can be an optionally substituted $C_1$-$C_{20}$ alkyl acyl or aryl acyl group, in particular a benzoyl or acetyl group.

Prior to the step of b), the process of the present application preferably comprises a step of isolating the silylated 5-azacytosine compound in solid form from the reaction mixture of the step a). For example, the isolation step may be accomplished by crystallizing silylated 5-azacytosine (more preferably by adding an effective amount of silylated 5-azacytosine seed crystals to promote the crystallization) and filtering off the crystallized silylated 5-azacytosine. Alternatively, the isolation step may be accomplished by evaporation of solvents in the reaction mixture of the step a). Utilizing crystallization to isolate the silylated compound is more preferred.

Preferably, the coupling step b) is conducted in the absence of a substantial amount, or more preferably, in the presence of a less than 1% by molar amount of the silyating agent relative to the molar amount of the silylated 5-azacytosine compound.

In accordance with one embodiment of the present invention, the process comprises a step of diluting the liquid reaction mixture comprising the protected 5-azacytosine nucleoside of formula (IV) obtained in the step b) with a second organic solvent. Preferably, at least a part of the first organic solvent is replaced by a second organic solvent so that the protected 5-azacytosine nucleoside of formula (IV) remains dissolved in the second organic solvent. More preferably, at least 60% by volume of the first organic solvent used in the step b) is subsequently removed prior to the step c). Preferably, the second organic solvent is a solvent having a higher boiling point than the first organic solvent.

The first organic solvent is a polar water soluble solvent, in particular acetonitrile. Preferably, the first organic solvent should be non-reactive and be stable in the presence of the catalyst used in the step b) and stable during the step of c). Since the first organic solvent, as noted above, may be mostly removed by evaporation after the step b) and before the step c), its boiling point should not be too high. On the other hand, since the step b) reaction may be conducted at a moderately high temperature, the first organic solvent should have a suitable high boiling point to allow the reaction mixture to be heated to the required reaction temperature without evaporating the first organic solvent.

The second organic solvent is preferably a polar aprotic solvent, more preferably, dimethylsulfoxide. The second organic solvent has a higher boiling point than the first organic solvent. It also should be stable during the step of c). Preferably, the second organic solvent has a boiling point that is high enough such that it will not be removed prior to the first organic solvent when a mixture of the first and second organic solvents is subjected to evaporation ("solvent swap/partial solvent swap"). The second organic solvent is also preferably polar enough such that it can keep the protected 5-azacytosine nucleoside of formula (IV) dissolved before and during the step of c), i.e., its high polarity preferably keeps the reaction of step c) homogenous, which was one innovation that we discovered. It is relatively difficult to reproduce the process of making 5-azacytosine nucleoside, when the step c) is not conducted in a fully homogenous solution. In addition, compared to a reaction in a heterogeneous slurry, keeping the step c) homogenous made the reaction much faster. Moreover, the purity of the final product following precipitation as a solid from step c) was superior when the step c) is carried out in a homogenous media due to the use of the polar high boiling point solvent.

Preferably, the 5-azacytosine nucleoside compound of formula I is azacitidine

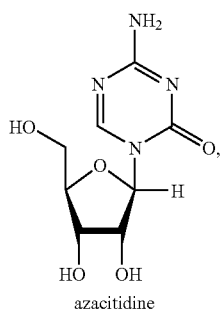

azacitidine and the protected D-ribofuranose of formula III is selected from the group consisting of

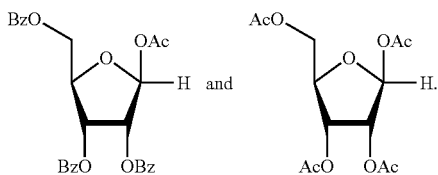

Alternatively and preferably, the 5-azacytosine nucleoside compound of formula I is decitabine

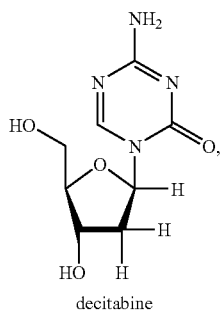

decitabine and the protected D-ribofuranose formula III is a 2-deoxy-D-ribofuranose as shown below

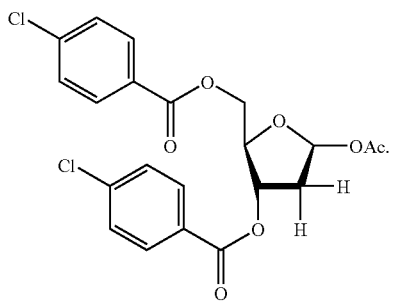

Preferably, the amount of the catalyst in the step b), in particular sulfonic acid, is less than one molar equivalent, in particular 10-30 mole percent, with respect to the molar amount of the protected D-ribofuranose of formula III.

The sulfonic acid catalyst is preferably trifluoromethane sulfonic acid.

The silylation agent is preferably hexamethyldisilizane.

Preferably, the step c) of the present application comprises deprotecting the protected 5-azacytosine nucleoside of formula (IV) in the presence of a basic deblocking agent. The basic deblocking agent is preferably a metal alkoxide, in particular sodium methoxide in methanol. The step c) is preferably conducted at a temperature between 20° C. to 30° C.

Preferably, the coupling step b) is conducted in the absence of a water immiscible solvent such as dichloromethane (DCM).

Preferably, the steps b) and c) are conducted in one reaction vessel.

As a preferred embodiment, the step c) is conducted in MeOH. More preferably, the step c) is conducted in a mixture of MeCN, DMSO and MeOH, in particular approximately 0-2 volumes of MeCN, 3 volumes of DMSO, and 2-3 volumes of MeOH.

The coupling step b) is preferably conducted at a temperature of between 40° C. to 80° C., more preferably, between 50° C. to 60° C. when the protected β-D-ribofuranose (III) is 1-O-acetyl-2,3,5-tri-O-benzoyl-β-D-ribofuranose.

Preferably, the process of the present application is free of a step of isolating the protected 5-azacytosine nucleoside of formula (IV) from a liquid mixture.

After the step c), the 5-azacytosine nucleoside of formula (I) may be isolated from the reaction mixture by precipitation with an organic solvent, followed by filtration. The 5-azacytosine nucleoside of formula (I) may also be purified by crystallization to furnish API grade material.

Compared to the prior art, the process in accordance with the present invention 1) does not require an aqueous workup; 2) does not require the addition of a large amount of catalyst; 3) steps b) and c) can be carried out more efficiently basically in one reactor vessel ("one pot"); 4) is time-saving; and/or 5) is amenable to manufacturing scale synthesis.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention

DETAILED DESCRIPTION OF THE PRESENTLY PREFERRED EMBODIMENTS

The following describes preferred embodiments of the present invention and should not be used to limit the scope of the present invention.

The present invention demonstrates a process of manufacture of azacytosine nucleosides that is extremely efficient and produces high yields and purity. A key aspect of the present invention relates to unexpected ability to use sulfonic acids in preferably substoichiometric amounts (relative to the silyl 5-azacytosine and protected sugar), as the catalyst in the coupling of silyl 5-azacytosines and protected 1-O-acyl-ribofuranose or 1-O-acyl-2-deoxy-ribofuranose sugars. This has not been described before for the manufacture of 5-azacytosine derived nucleosides and the use of less than one equivalent amount of a sulfonic acid ultimately leads to a series of major process improvements over those in the prior art processes, such as being able to omit an aqueous work-up step and more efficient use of reaction vessels. The new process is industrially applicable and has been scaled into production equipment obtaining a significantly higher yield of azacitidine than that reported in the prior art.[2,3,7]

According to an embodiment of the present invention, a process for the preparation of 5-azacytosine nucleosides and their derivatives of the formula:

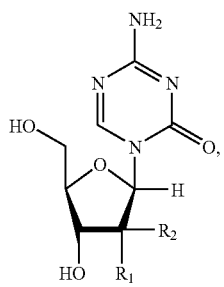

wherein $R_1$ is hydrogen, hydroxy or fluorine; $R_2$ is hydrogen or fluorine is demonstrated. Silyl 5-azacytosine is coupled with protected (blocked) D-ribose sugars under the catalysis of sulfonic acids preferably in less than one equivalent. Upon completion of the coupling, the reaction mixture is used in the next synthetic step without the addition of water or any aqueous base solution, which is harmful to the 5-azacytosine moiety. A higher boiling solvent is added such that the protected 5-azacytosine nucleosides remains in a homogeneous solution and a deblocking agent such as sodium methoxide in methanol can be added in order to form the deprotected product and remove the strong acid catalyst. Following precipitation the product can then be collected by filtration in high yield and purity. In this manner, a very efficient commercial process for the large scale preparation of 5-azacytosine nucleotides can be derived.

In one embodiment of the present invention, the inventors specifically developed a process in which silylated 5-azacytosine is reacted with hydroxy-protected β-D-ribofuranose, 2-deoxy-α,β-D-ribofuranose, 2-deoxy-2-fluoro-β-D-ribofuranose or 2-deoxy-2,2-difluoro-β-D-ribofuranose in the presence of a substoichiometric amount of trifluoromethane sulfonic acid (TfOH). The process need not be limited to the use of substoichiometric quantities of TfOH, however, of great impact, the use of a substoichiometric amount of TfOH allows for the complete omission of the standard aqueous work-up that is used in other methods.[6,7,8,9,12] The catalyst is conveniently quenched in the deprotection step itself and is removed from the precipitated product in the filtrate. This allows the coupling reaction, the quench of the catalyst and the deprotection reaction to all be carried out in one reactor so that the exposure of the water-sensitive products to water is completely avoided. Thus, it is apparent that the use of a substoichiometric amount of the coupling catalyst has a large impact on the whole process. The complete omission of an aqueous work-up is a significant improvement over that of other methods particularly on a manufacturing scale where processing duration are much longer than on the laboratory scale. Yield losses that can occur due to hydrolysis of the water sensitive glycosylated 5-azacytosine ring during aqueous work-ups is avoided, allowing for better overall quality and yield.

The inventors discovered that addition of a polar solvent such as DMSO following the coupling reaction makes the deprotection (deblocking) reaction, which is preferably conducted in a solution of NaOMe in MeOH, proceed rapidly as a homogeneous solution. This homogeneous solution is a mixture of MeCN, DMSO and MeOH. When the deprotection step is complete, the addition of a larger amount of MeOH causes the crude nucleoside API product to precipitate and it can be collected directly. Azacitidine of API grade (≧99.0% HPLC purity, no impurities≧0.1%) was obtained in 85~90% recovery yield following only a single purification step. The use of MeCN as a reaction solvent in the coupling step and the absence of an aqueous work-up eliminated the need for a costly solvent swap to a water non-miscible solvent such as is provided in other references.[7,14]

The process in accordance with embodiments of the present invention encompasses several key improvements upon other methods. The use of a strong, sulfonic acid as a catalyst instead of tin chloride or trimethylsilyl trifluoromethane sulfonate (also known as TMS-Triflate, TMSOTf) enables effective coupling of silyl 5-azacytosines with protected sugars. A number of alkyl or aryl sulfonic acids can be employed but most preferably, trifluoromethane sulfonic acid is suggested. The catalyst can be employed in less than one molar equivalent to one equivalent in a range of 10% to 100%, most preferable, 20% with respect to the molar amount of the protected D-ribofuranose. The silyl 5-azacytosine may contain any suitable silyl groups, but most preferred is trimethylsilyl. The blocked sugar may contain any suitable hydroxyblocking group such as either alkyl or aryl acyl groups. The solvent is any suitable organic solvent preferably a water miscible organic solvent and most preferably acetonitrile.

Upon completion of the coupling reaction, preferably no aqueous conditions are employed and instead a suitable higher boiling polar solvent is added such that the contents of the reactor remain solubilized and the solvent is stable to the deblocking conditions. Suitable solvents can be sulfoxides, amides, glycols and the such. Most preferably the solvent is DMSO. Finally, the process is completed by the addition of a deblocking agent followed by precipitation of the product which can be collected by filtration. If the blocking groups are acyl, alkoxides are the preferred deblocking agents and are generally added in an alcohol solution. Sodium methoxide in methanol is typically used. Upon completion of this step, the product is precipitated by the addition of an anti-solvent such as methanol and can be collected by filtration in high yield and purity. While a number of useful nucleosides can be synthesized by this process, it is most suitable for the synthesis of azacitidine.

The following examples are provided for the purpose of further illustration only and are not intended to be limitations on the disclosed invention.

Example 1

Preparation of 2-[(trimethylsilyl)amino]-4-[(trimethylsilyl)oxy]-s-triazine(silyl 5-azacytosine)

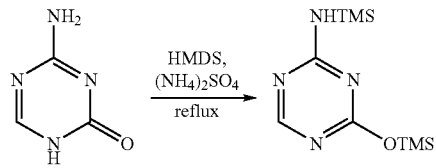

A mixture of 5-azacytosine (7.33 Kg), HMDS (33.9 Kg) and ammonium sulfate (0.44 Kg) was heated at reflux (about 115-135° C.) and stirred for 16 hours. After the reaction was complete, the slurry was cooled to 118° C. and then filtered through a bed of celite and rinsed with HMDS (5.6 Kg). The silylated 5-azacytosine solution was cooled to 35° C. and the solution was cooled to 18° C., stirred at 18° C., for not less than 6.5 hours and then filtered. The solid was washed twice with HMDS (5.6 Kg each) and dried under vacuum at ≦70° C. for 9.5 hours to obtain 14.19 Kg of white silyl 5-azacytosine (87%).

Example 2

Coupling of Silyl 5-Azacytosine to Sugar and Deprotection

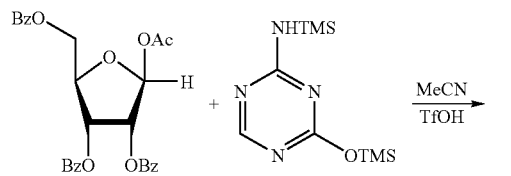

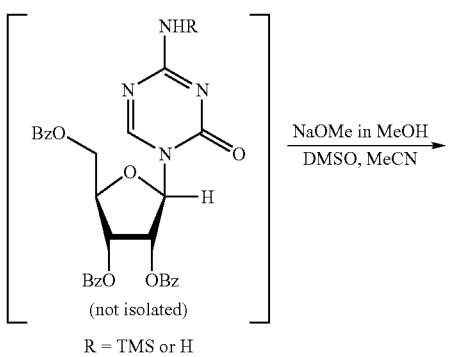

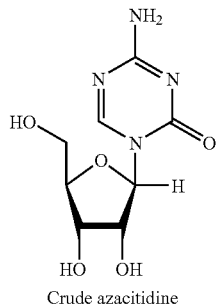

Crude azacitidine

A mixture of 2-[(trimethylsilyl)amino]-4-[(trimethylsilyl)oxy]-s-triazine (4.5 Kg), 1-O-acetyl-2,3,5-tri-O-benzoyl-β-D-ribofuranose (8.8 Kg), anhydrous MeCN (34.6 Kg) and TfOH (600 g) were heated at 55° C. for 12.5 hours. The reaction mixture was cooled to 45° C., DMSO (29 Kg) was added, and the MeCN was evaporated at an internal temperature of <50° C. under vacuum until about 54 L of the solution. The solution was cooled to 23° C. MeOH (13.9 Kg) was added followed by a solution of 30% NaOMe in MeOH solution (2.5 Kg) that was pre-diluted with MeOH (7.0 Kg). The solution was stirred at 23° C. for 35 minutes. When the reaction was complete MeOH (90.4 Kg) was added and the resulting slurry was stirred at 22° C. for 3 hours and 10 minutes and was then filtered and washed three times with MeOH (7.0 Kg each). The cake was dried under vacuum at below 70° C. for 9 hours and 20 minutes to give 3.2 Kg of 98.89% purity crude azacitidine (71% yield based on 1-O-acetyl-2,3,5-tri-O-benzoyl-β-D-ribofuranose).

Example 3

Purification of Crude Azacitidine

Crude azacitidine (3.2 Kg) was dissolved in DMSO (11.8 Kg) at 20-40° C., filtered and the collected solids were rinsed with DMSO (10.1 Kg). The filtrate was cooled to 20-25° C. and MeOH (9.7 Kg) was added over a 30-minute period and then azacitidine seed crystals (30.6 g) were added and the mixture was stirred for about 1 hour at 23° C. More MeOH was added over a 4-hour and 13-minute period and the mixture was stirred at 20-25° C. for at least 10 hours, filtered and washed three times with MeOH (10 Kg each). The filter cake was dried under vacuum at less than ≦70° C. for 33 hours to furnish 2.6 Kg of API grade azacitidine (86% yield based on crude azacitidine).

Example 4

One-Pot Process for Preparation of Crude Decitabine

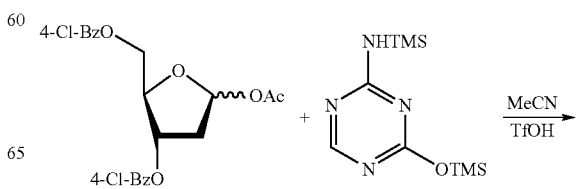

-continued

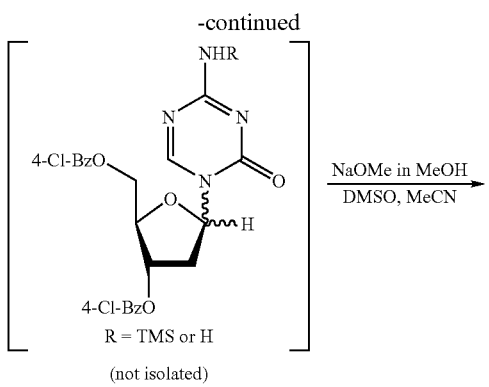

(not isolated)

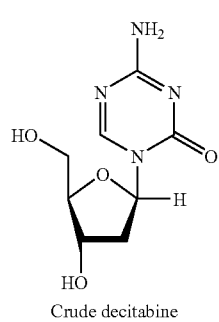

Crude decitabine

A mixture of MeCN (45 mL), 1-O-acetyl-3,5-di-O-(4-chlorobenzoyl)-2-deoxy-D-ribofuranose (3.0 g), 2-[(trimethylsilyl)amino]4-[(trimethylsilyl)oxy]-s-triazine (1.78 g) and TfOH (0.5 g) were stirred at about 0° C. for 24 hours. DMSO (6 mL) was added and the mixture was evaporated at 30~50° C. under reduced pressure to remove the MeCN. A 29% solution of MeONa in MeOH (1.8 g, 9.9 mmol, 1.5 eq.) was added with stirring at about 20~25° C. After the reaction was complete, MeOH was added to effect precipitation and the solid was filtered, washed and dried to give crude decitabine. API grade decitabine (>99.0 HPLC purity) is prepared by the recrystallization of crude decitabine from MeOH, followed by three washes with MeOH and drying at 40° C. under vacuum.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, reaction conditions other than the particular conditions as set forth herein above may be applicable as a consequence of variations in the reagents or methodology to prepare the compounds from the processes of the invention indicated above. It is intended, therefore, that the invention be defined by the scope of the claims which follow and that such claims be interpreted as broadly as is reasonable.

We claim:
1. A process for the preparation of a 5-azacytosine nucleoside compound of formula I:

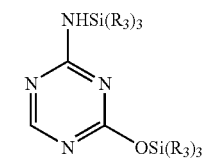

I wherein $R_1$ is hydrogen, hydroxy or halogen; $R_2$ is hydrogen or halogen comprising:
a. reacting 5-azacytosine with a silylating agent to produce a reaction mixture containing a silylated 5-azacytosine of formula II:

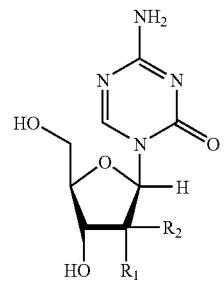

II wherein each of $R_3$ is independently optionally substituted $C_1$-$C_{20}$ alkyl group or aryl group;
b. coupling the silylated 5-azacytosine of formula II with a protected D-ribofuranose of formula III:

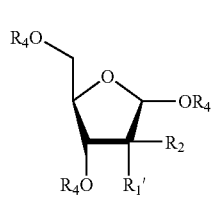

III wherein $R_1'$ is hydrogen, halogen or $OR_4$; $R_4$ represents a hydroxyl-protecting group; in a first organic solvent and in the presence of a sulfonic acid catalyst to obtain a solution of a protected 5-azacytosine nucleoside of formula IV:

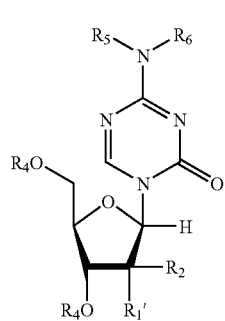

IV wherein each of $R_5$ and $R_6$ is independently hydrogen or $Si(R_3)_3$, $R_3$ is an optionally substituted $C_1$-$C_{20}$ alkyl or aryl group, and $R_1'$ and $R_2$ are as defined above; and c. converting the protected 5-azacytosine nucleoside of formula (IV) to the 5-azacytosine nucleoside of formula (I);

wherein prior to the step of b), the silylated 5-azacytosine compound is isolated in a solid form from the reaction mixture of the step a).

2. The process of claim 1 wherein said protected D-ribofuranose of formula III is selected from the group consisting of

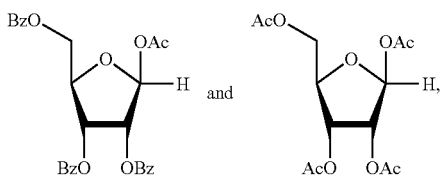

and the 5-azacytosine nucleoside compound of formula I is azacitidine

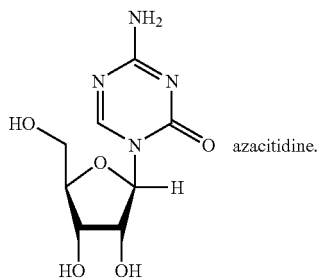

azacitidine.

3. The process of claim 1 wherein said protected D-ribofuranose formula III is a 2-deoxy-D-ribofuranose as shown below

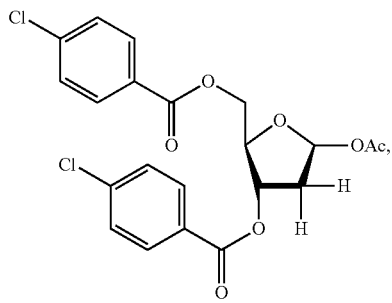

and the 5-azacytosine nucleoside compound of formula I is decitabine

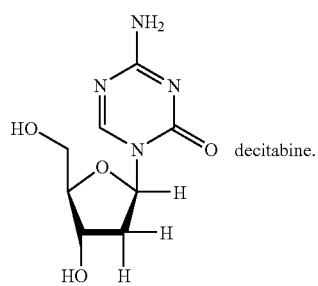

decitabine.

4. The process of claim 1 wherein the first organic solvent is a polar water soluble solvent.

5. The process of claim 1 wherein the first organic solvent is acetonitrile.

6. The process of claim 1 wherein the sulfonic acid is trifluoromethane sulfonic acid.

7. The process of claim 1 wherein the silylation agent is hexamethyldisilizane.

8. The process of claim 1 wherein the step c) comprises deprotecting the protected 5-azacytosine nucleoside of formula (IV) in the presence of a basic deblocking agent.

9. The process of claim 8 wherein the basic deblocking agent is a metal alkoxide.

10. The process of claim 9 wherein the metal alkoxide is sodium methoxide in methanol.

11. The process of claim 1 wherein the coupling step b) is conducted in the absence of a water immiscible solvent.

12. The process of claim 1 wherein the steps b) and c) are conducted in one reaction vessel.

13. The process of claim 1 wherein the process is free of a step of isolating the protected 5-azacytosine nucleoside of formula (IV) from a liquid mixture.

14. The process of claim 1 wherein the hydroxyl-protecting group is an optionally substituted $C_1$-$C_{20}$ alkyl acyl or aryl acyl group.

15. The process of claim 1 wherein the step c) is conducted at a temperature of 20° C. to 30° C.

16. A process for the preparation of a 5-azacytosine nucleoside compound of formula (I):

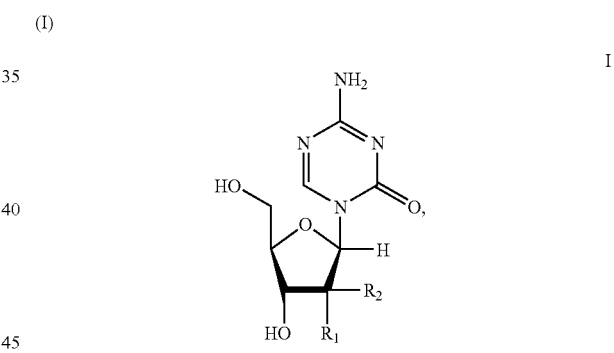

wherein $R_1$ is hydrogen, hydroxy or halogen; $R_2$ is hydrogen or halogen; and the process comprises:

i) forming a homogenous solution comprising at least a polar aprotic solvent and a protected 5-azacytosine nucleoside of formula (IV):

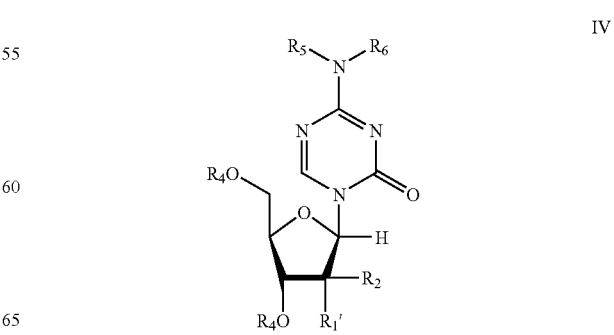

wherein each of $R_5$ and $R_6$ is independently hydrogen or $Si(R_3)_3$, and $R_3$ is an optionally substituted $C_1$-$C_{20}$ alkyl group or aryl group, and $R_1'$ and $R_2$ are as defined above; and ii) converting the protected 5-azacytosine nucleoside of formula (IV) to the 5-azacytosine nucleoside of formula (I) in the homogenous solution.

17. The process of claim 16 wherein prior to the step ii) the process is free of a step carried out in the presence of a substantial amount of water.

18. A process for the preparation of a 5-azacytosine nucleoside compound of formula I:

(I)

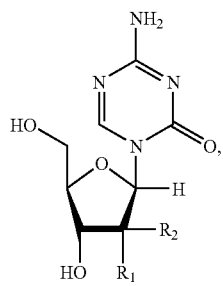

wherein $R_1$ is hydrogen, hydroxy or halogen; $R_2$ is hydrogen or halogen comprising:

a. reacting 5-azacytosine with a silylating agent to produce a reaction mixture containing a silylated 5-azacytosine of formula II:

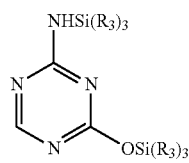

wherein each of $R_3$ is independently optionally substituted $C_1$-$C_{20}$ alkyl group or aryl group;

b. coupling the silylated 5-azacytosine of formula II with a protected D-ribofuranose of formula III:

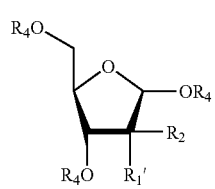

wherein $R_1'$ is hydrogen, halogen or $OR_4$; $R_4$ represents a hydroxyl-protecting group; in a first organic solvent and in the presence of a sulfonic acid catalyst to obtain a solution of a protected 5-azacytosine nucleoside of formula IV:

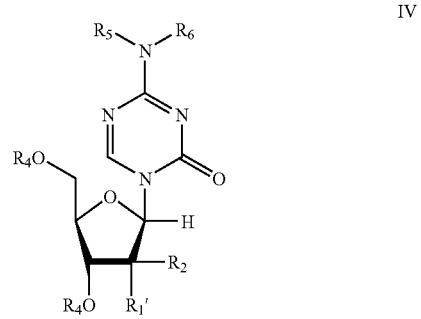

wherein each of $R_5$ and $R_6$ is independently hydrogen or $Si(R_3)_3$, $R_3$ is an optionally substituted $C_1$-$C_{20}$ alkyl or aryl group, and $R_1'$ and $R_2$ are as defined above; and c. converting the protected 5-azacytosine nucleoside of formula (IV) to the 5-azacytosine nucleoside of formula (I);

wherein the coupling step b) is conducted in the presence of less than 1% by molar amount of the silyating agent relative to the molar amount of the silylated 5-azacytosine compound.

19. A process for the preparation of a 5-azacytosine nucleoside compound of formula I:

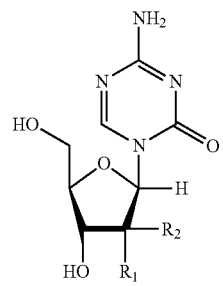

wherein $R_1$ is hydrogen, hydroxy or halogen; $R_2$ is hydrogen or halogen comprising:

a. reacting 5-azacytosine with a silylating agent to produce a reaction mixture containing a silylated 5-azacytosine of formula II:

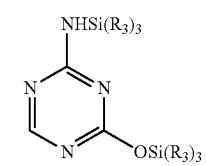

wherein each of $R_3$ is independently optionally substituted $C_1$-$C_{20}$ alkyl group or aryl group;

b. coupling the silylated 5-azacytosine of formula II with a protected D-ribofuranose of formula III:

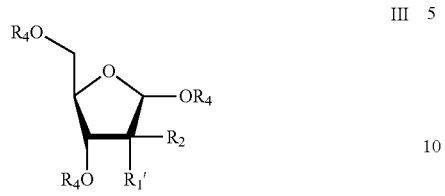

wherein $R_1'$ is hydrogen, halogen or $OR_4$; $R_4$ represents a hydroxyl-protecting group; in a first organic solvent and in the presence of a sulfonic acid catalyst to obtain a solution of a protected 5-azacytosine nucleoside of formula IV:

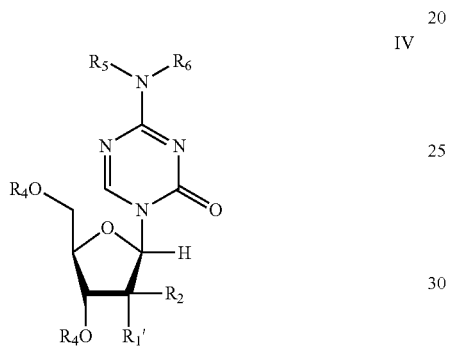

wherein each of $R_5$ and $R_6$ is independently hydrogen or $Si(R_3)_3$, $R_3$ is an optionally substituted $C_1$-$C_{20}$ alkyl or aryl group, and $R_1'$ and $R_2$ are as defined above; and c. converting the protected 5-azacytosine nucleoside of formula (IV) to the 5-azacytosine nucleoside of formula (I);

wherein the process comprises a step of diluting the solution of the protected 5-azacytosine nucleoside of formula (IV) obtained in the step b) with a second organic solvent, and wherein second organic solvent is a polar aprotic solvent having a higher boiling point than the first organic solvent.

20. The process of claim 19 wherein the second organic solvent is dimethylsulfoxide.

21. A process for the preparation of a 5-azacytosine nucleoside compound of formula I:

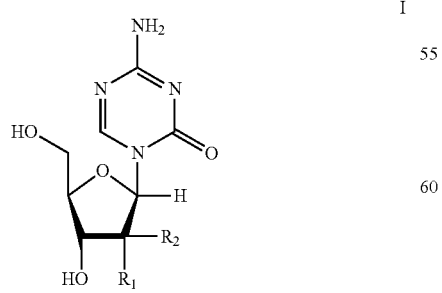

wherein $R_1$ is hydrogen, hydroxy or halogen; $R_2$ is hydrogen or halogen comprising:

a. reacting 5-azacytosine with a silylating agent to produce a reaction mixture containing a silylated 5-azacytosine of formula II:

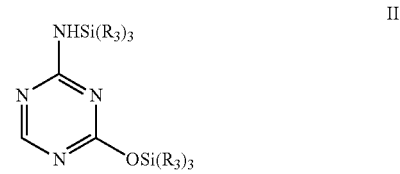

wherein each of $R_3$ is independently optionally substituted $C_1$-$C_{20}$ alkyl group or aryl group;

b. coupling the silylated 5-azacytosine of formula II with a protected D-ribofuranose of formula III:

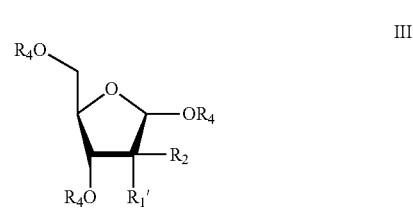

wherein $R_1'$ is hydrogen, halogen or $OR_4$; $R_4$ represents a hydroxyl-protecting group; in a first organic solvent and in the presence of a sulfonic acid catalyst to obtain a solution of a protected 5-azacytosine nucleoside of formula IV:

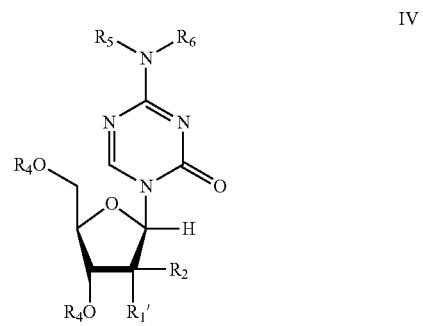

wherein each of $R_5$ and $R_6$ is independently hydrogen or $Si(R_3)_3$, $R_3$ is an optionally substituted $C_1$-$C_{20}$ alkyl or aryl group, and $R_1'$ and $R_2$ are as defined above; and c. converting the protected 5-azacytosine nucleoside of formula (IV) to the 5-azacytosine nucleoside of formula (I);

wherein the amount of the sulfonic acid is less than one molar equivalent with respect to the protected D-ribofuranose of formula III.

22. The process of claim 21 wherein the amount of the sulfonic acid is 10-30 mole percent of the molar amount of the protected D-ribofuranose of formula III.

23. A process for the preparation of a 5-azacytosine nucleoside compound of formula I:

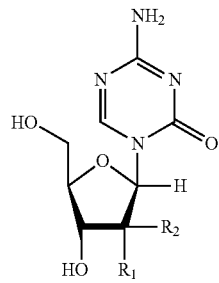

wherein $R_1$ is hydrogen, hydroxy or halogen; $R_2$ is hydrogen or halogen comprising:

a. reacting 5-azacytosine with a silylating agent to produce a reaction mixture containing a silylated 5-azacytosine of formula II:

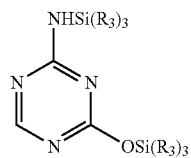

wherein each of $R_3$ is independently optionally substituted $C_1$-$C_{20}$ alkyl group or aryl group;

b. coupling the silylated 5-azacytosine of formula II with a protected D-ribofuranose of formula III:

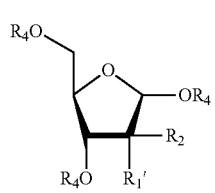

wherein $R_1'$ is hydrogen, halogen or $OR_4$; $R_4$ represents a hydroxyl-protecting group; in a first organic solvent and in the presence of a sulfonic acid catalyst to obtain a solution of a protected 5-azacytosine nucleoside of formula IV:

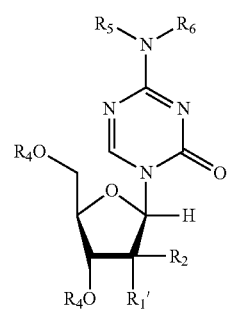

wherein each of $R_5$ and $R_6$ is independently hydrogen or $Si(R_3)_3$, $R_3$ is an optionally substituted $C_1$-$C_{20}$ alkyl or aryl group, and $R_1'$ and $R_2$ are as defined above; and c. converting the protected 5-azacytosine nucleoside of formula (IV) to the 5-azacytosine nucleoside of formula (I);

wherein the process is free of an aqueous work-up step to quench or remove the sulfonic acid catalyst.

* * * * *